United States Patent [19]
Swierkowski

[11] Patent Number: 5,877,580
[45] Date of Patent: Mar. 2, 1999

[54] MICROMACHINED CHEMICAL JET DISPENSER

[75] Inventor: Steve P. Swierkowski, Livermore, Calif.

[73] Assignee: Regents of the University of California, Oakland, Calif.

[21] Appl. No.: 772,639

[22] Filed: Dec. 23, 1996

[51] Int. Cl.$^6$ .................................................. H01L 41/08
[52] U.S. Cl. ........................................ 310/328; 310/331
[58] Field of Search ........................... 310/328, 330–333; 347/68–72

[56] References Cited

U.S. PATENT DOCUMENTS

| | | | |
|---|---|---|---|
| 3,848,118 | 11/1974 | Rittberg | 239/101 |
| 4,032,929 | 6/1977 | Fischbeck et al. | 346/140 R |
| 4,115,789 | 9/1978 | Fischbeck | 346/140 R |
| 4,639,631 | 1/1987 | Chason et al. | 310/344 |
| 4,680,595 | 7/1987 | Cruz-Uribe et al. | 346/140 R |
| 4,812,856 | 3/1989 | Wallace | 347/89 |
| 5,411,602 | 5/1995 | Hayes | 148/23 |
| 5,415,679 | 5/1995 | Wallace | 75/331 |
| 5,448,126 | 9/1995 | Eda et al. | 310/344 X |
| 5,475,279 | 12/1995 | Takeuchi et al. | 310/331 |
| 5,512,793 | 4/1996 | Takeuchi et al. | 310/328 |
| 5,617,127 | 4/1997 | Takeuchi et al. | 347/71 |

Primary Examiner—Mark O. Budd
Attorney, Agent, or Firm—L. E. Carnahan

[57] ABSTRACT

A dispenser for chemical fluid samples that need to be precisely ejected in size, location, and time. The dispenser is a micro-electro-mechanical systems (MEMS) device fabricated in a bonded silicon wafer and a substrate, such as glass or silicon, using integrated circuit-like fabrication technology which is amenable to mass production. The dispensing is actuated by ultrasonic transducers that efficiently produce a pressure wave in capillaries that contain the chemicals. The 10–200 μm diameter capillaries can be arranged to focus in one spot or may be arranged in a larger dense linear array (~200 capillaries). The dispenser is analogous to some ink jet print heads for computer printers but the fluid is not heated, thus not damaging certain samples. Major applications are in biological sample handling and in analytical chemical procedures such as environmental sample analysis, medical lab analysis, or molecular biology chemistry experiments.

20 Claims, 2 Drawing Sheets

MICROMACHINED CHEMICAL JET DISPENSER

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to fluid dispensers, particularly to dispensers for chemical fluid samples, and more particularly to a micromachined chemical jet dispenser whereby chemical fluid samples can be precisely ejected in size, location, and time.

Many chemistry experiments require the manipulation of small chemical samples in large numbers. Often crude pipetting or wet needle drop transferring is done with robotic drop handlers for increased parallelism.

Micromachining of various components, particularly silicon, is being actively pursued in various fields of technology. This micromachining technology is generally referred to as micro-electro-mechanical systems (MEMS); and one of the later applications of this technology is the extremely successful computer printer ink jet print head, which is a silicon based microstructure based on the heated bubble jet concept.

Many applications exist for a highly improved method of dispensing miniature chemical droplets where heating is not allowed; and new opportunities will arise in the fields of molecular biology, clinical laboratories, environmental laboratories, and the chemical industry. Thus, there is a need to enable dispensing of fluid chemical samples rapidly as well as precisely in location, size, and time under computer control. Miniaturized chemical experiments by the thousands can be rapidly done with such a dispensing device, this being amenable to multiple processes requiring many combinatorial and/or sequential chemical reactants to be combined or just placed, separately or jointly, for subsequent processing or analysis. For example, the human genome program has ideal applications for such a dispenser. The arraying of transformed bacterial colonies carrying DNA of chromosome 19 onto 8×12 cm nylon filters is a significant bottleneck (currently >3 hours for 45 nylon filters) to the research, as it is currently done with a slow robotic needle dipping method. Other biomedical applications for such a dispenser include synthesis of DNA oligomers and injection into multichannel electrophoresis experiments.

The above-mentioned needs and resolution of the above dispensing problems are satisfied by the present invention, which constitutes a micromachined chemical jet dispenser. This invention fills this type of need in a manner similar to the above-referenced ink jet print heads but without heat damage to the samples. The device of this invention enables the production of large (~100), dense linear arrays (~50 channels/cm) in a manner that is stackable, thus further enabling the generation of two dimensional arrays of chemical samples, with micro precision; droplets in the range of 10–200 $\mu$m are feasible. The efficiency of the drop dispensing device of this invention is much greater than current non-monolithic technologies can allow, and it is ideally suited to computer control and robotics systems.

SUMMARY OF THE INVENTION

It is an object of the present invention to provide a chemical fluid dispenser.

A further object of the invention is to provide a dispenser for ejection of chemical fluid samples precisely in size, location, and time.

A further object of the invention is to provide a micromachined chemical jet dispenser.

A further object of the invention is to provide a microdrop transfer device.

Another object of the invention is to provide a micromachined chemical jet dispenser actuated by ultrasonic transducers that produce a pressure wave in capillaries that contain the chemicals.

Another object of the invention is to provide a chemical sample dispenser utilizing a bonded silicon member and a glass or silicon substrate, wherein fluid wells are formed in the silicon member and capillaries (chemical jets) are formed in the glass substrate or the silicon member.

Another object of the invention is to provide a micromachined chemical fluid dispenser which utilizes a plurality of piezoelectric drivers to precisely eject fluid in size, location, and time.

Another object of the invention is to provide a chemical fluid dispenser wherein the fluid is not heated.

Other objects and advantages of the invention will become apparent from the following description and accompanying drawings. The invention involves a micromachined fluid dispenser which is particularly adapted for chemical fluid samples that need to be precisely ejected in size, location and time. The dispensing of the fluid is carried out by ultrasonic transducers (piezoelectric drivers) that efficiently produce a pressure wave in capillaries that contain the chemicals. The dispenser is basically composed of a silicon member bonded to a glass (or silicon) substrate, the substrate containing the capillaries, and the silicon member including a plurality of fill wells, dead wells, and driven wells, each formed by micromachining of the silicon member and aligned with the capillaries in the glass substrate. The ultrasonic transducers or drivers are positioned over the driven wells to force fluid through the capillaries when activated. The silicon member may be provided with a silicon nitride or silicon cap layer and may include acoustic absorption layers. Also, a glass layer may be positioned over each of the dead wells of the silicon member to strengthen the thin silicon wall. The piezoelectric drivers enable the device to have both drop-on-demand or continuous flow capabilities. If desired, the capillaries may be formed on the bottom surface of the silicon member.

The micromachined dispenser of the present invention has many applications such as: 1) biological sample handling where large numbers of small samples are processed, especially where precision and robotics apply; 2) examples including DNA gene spotter for human genome mapping; 3) injection of samples into other apparatus such as multichannel electrophoresis experiments; 4) replacement for human pipette transfers of many different kinds; 5) environmental analytical chemical analysis; e.g. precision titration; and 6) computer driven search procedures, i.e., miniature chemical experiments by the thousands seeking certain reactions. This is very amenable to multiple processes requiring many combinatorial and/or sequential chemical reactants to be combined or just placed precisely, separately or jointly, for subsequent processing. Also, the dispenser can be used in ink jet computer printing heads having a no-heating requirement.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

Figure 1:
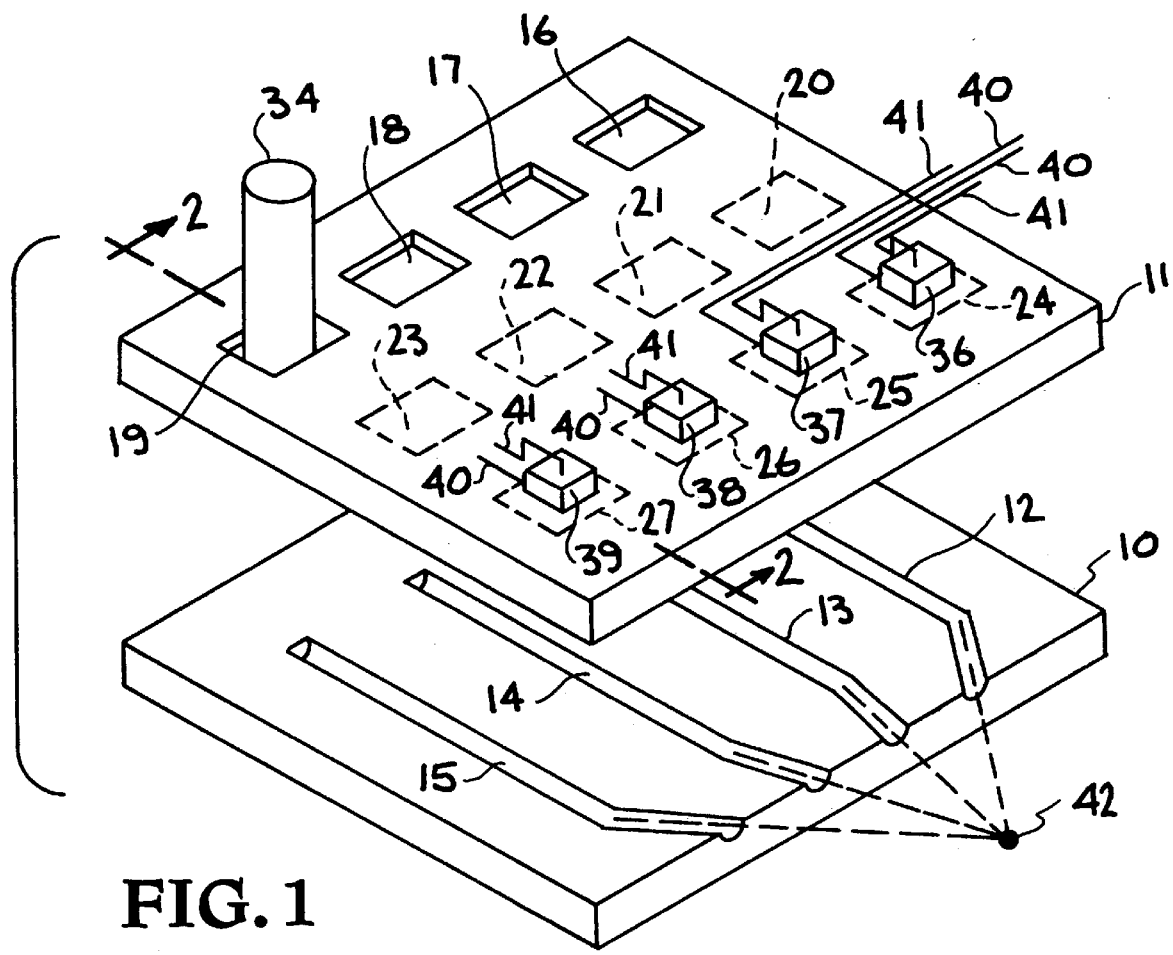
FIG. 1 is an exploded view generally illustrating the principle components of an embodiment of the micromachining chemical jet dispenser of the present invention.

The invention is directed to a micromachined chemical jet dispenser wherein samples can be precisely ejected in size, location, and time. The fluid dispenser functions similar to the above-referenced ink jet printer heads but without heat damage to the samples. The dispensing of fluids is actuated by ultrasonic transducers that produce a pressure wave in capillaries that contain the fluids. The 10–200 $\mu$m diameter capillaries can be arranged to focus in one spot or arranged in a larger linear array (~200 capillaries). The construction of the dispenser enables the production of large, dense linear arrays (~50 channels/cm) in a manner that is stackable, thus further enabling the generation of two dimensional arrays of chemical sample, with micron precision. The dispenser, as illustrated in the drawings, is basically composed of three components: 1) a substrate, composed of glass, for example, having capillaries formed therein; 2) a member, composed of silicon, for example, having machined "fill", "dead", and "driven" fluid wells therein and bonded to the substrate; and 3) piezoelectric drivers (ultrasonic transducers) mounted on the member and positioned over the machined "driven" fluid wells to force fluid through the capillaries in the substrate.

Key features of the present invention include:

1. Provides a large planar surface for the pressure actuator and the ejecting of the droplets in the plane of this surface from capillaries and provides adequate area for piezoelectrics, accurate drop trajectories, and high linear density. This orthogonal geometry allows for high power actuation and minimal acoustic cross talk, which improves accuracy and precision of droplet size as well as trajectory. Acoustic absorption layers may be added to the silicon member on both sides to minimize cross talk, both transverse and in the plane of the member.

2. Uses anisotropically etched silicon members to produce fluid wells capped, for example, by a silicon nitride or silicon cap layer that is strong but compliant. This enables the "dead wells" which act as a large compliant fluid mass that can absorb reverse hydraulic shocks and also can function as a refill, reverse fill, and pressure regulating mechanism.

3. Enables a microdrop to be sucked up, moved, and then ejected, thereby functioning as a microdrop transfer device.

4. The silicon cap layer can effectively serve as a wiring plane for the bonded actuators; it is also suitable for integration of thin film piezoelectrics and subsequent patterning.

5. The device utilizes an electric drive system for drop-on-demand or continuous flow. For drops(s)-on-demand mode, a resonant biased drive is disclosed where a steady state, below-threshold oscillation bias is provided to set up standing waves in the fluid (tending to produce uniform droplet sizes at constant frequency); a pulsed ejection excitation is added in sychronism to the oscillation bias, to eject a pulse when desired. For additional cross talk suppression, perhaps needed for very large droplets, it should be possible to electronically compensate by applying an inhibitor pulse to the adjacent channels.

Figure 3:
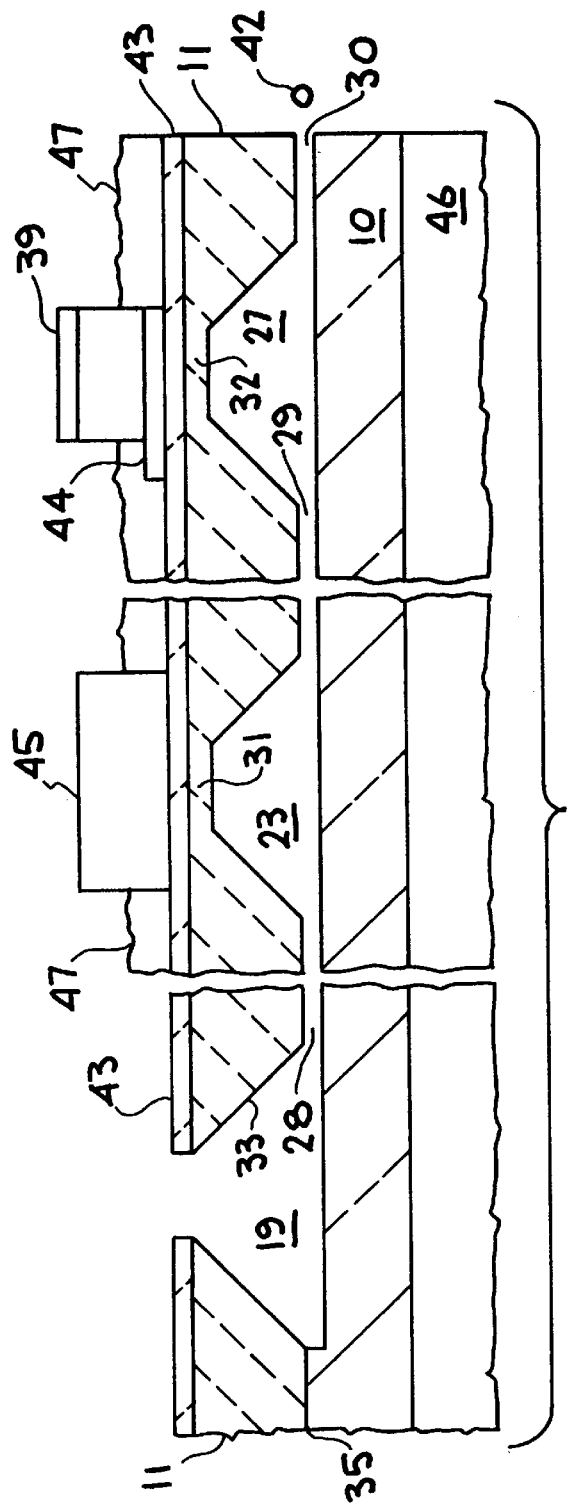
FIG. 3 is an enlarged cross-sectional view of an embodiment of the silicon member of the FIG. 1 dispenser, illustrating various layers which may be utilized in the dispensing device.
Figure 4:
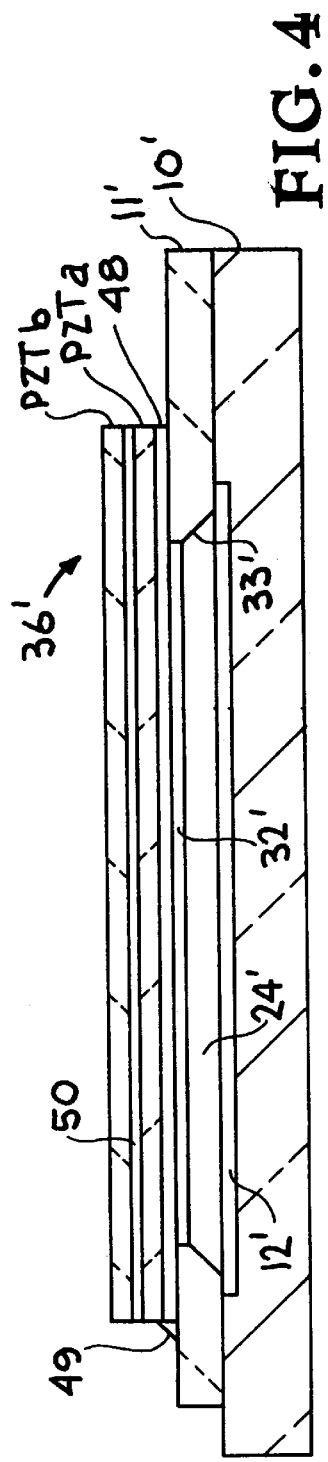
FIG. 4 is an enlarged cross-sectional view of an embodiment of a piezoelectric driver of the FIG. 1 embodiment.

Construction of the micromachined chemical jet dispenser is based on several common fabrication procedures used in micro-electro-mechanical systems (MEMS) technology. First, standard spin coated positive photoresists (PR) and contact lithography from standard 100 mm (4×4 inch) photomasks is used. The preferential etching of [100] oriented silicon, that is double side polished, is used to form the fluid wells or reservoirs in this microfluidics device; these reservoirs are referred to as the fill wells, dead wells, and driven wells. The preferential etching of the silicon leaves a square well in the silicon with a very thin (not greater than 100 $\mu$m) membrane or wall of silicon left. Where a silicon nitride layer is used, the membrane can be reduced to near zero thickness. The silicon membrane of the driven well is actuated by a bonded piezoelectric transducer that deflects the membrane inward, compresses the fluid in the driven well, and ejects a micro droplet out the exit nozzle. The piezoelectric transducers are mounted with conductive epoxy to gold pads that are evaporated onto the silicon opposite the etched wells, on the outside of the silicon wafer; extra metal is deposited for contacts and other alignment features to be described hereinafter. The micro capillaries connecting the reservoirs to the inlet and exit nozzles are etched in the glass substrate, which may be composed of Pyrex in this embodiment, for example. This 1 mm thick glass is anodically bonded to the standard thickness (375 $\mu$m) silicon member or wafer. This anodic bonding method is well established and known to sustain pressures in excess of 1.4 MPa (200 psi). Most of the fabrication is of the type used in the MEMS or integrated circuit (IC) industry and yields a precision integrated structure. The piezoelectric actuator was chosen for its high pressure, small displacement attributes as well as its commercial availability in high quality, thin plate form. Commercial PZT (lead zirconium titanate) plates, that are plated and poled, are used to make a bimorphic actuator, as illustrated in FIG. 4. The device may have parallel rather than converging exit nozzles as shown in FIG. 1. It may also have a small glass support layer bonded over the dead wells, to prevent this well's membrane or wall from bursting during operation, as shown in FIG. 3. In addition to glass, the substrate may be composed of silicon, quartz, or metal; and instead of silicon the member may be composed of anisotropically etched crystals such as germanium or gallium arsenide.

Referring now to the drawings, the embodiment of FIG. 1 generally comprises a substrate 10 and member or wafer 11. The substrate 10 is composed, for example, of glass, such as Corning 7740 type, commonly known as Pyrex, having a thickness of 1 mm and provided on the upper surface a plurality of micro-capillaries 12, 13, 14, and 15 having a diameter of 10–200 $\mu$m. The capillaries may vary in diameter along the length thereof as described hereinafter.

Figure 2:
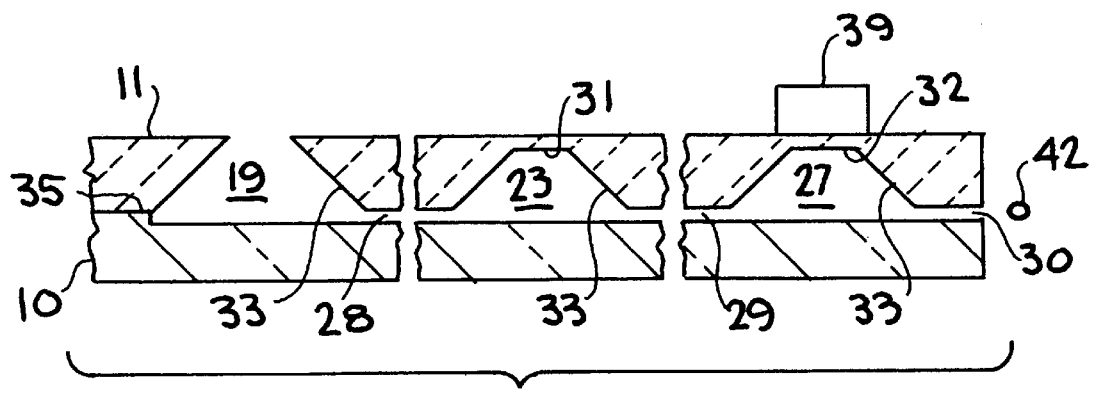
FIG. 2 is a partial cross-sectional view of the embodiment of FIG. 1 in a non-exploded arrangement and taken along the line 2—2 of FIG. 1.

The member 11 is composed, for example, of [100] oriented silicon that is double side polished having a thickness of 375 $\mu$m. The member 11 is provided with four fill wells 16, 17, 18, and 19, four dead wells or high resistance channels 20, 21, 22, and 23, and four driven wells 24, 25, 26, and 27, with fill wells 16–19 connected to dead wells 20–23 via orifices or passages 28 (only one shown), and dead wells 20–23 being connected to driven wells 24–27 via orifices or opening 29 (only one shown), with driven wells 24–27 having exit orifices, nozzles, or passages 30 (only one shown), as illustrated in FIG. 2. Orifices 28, 29, and 30 are formed by capillary 15, for example, when silicon member 11 is bonded to substrate 10. Fill wells 16–19 are preferentially etched in silicon member 11 so as to provide openings in the upper surface of silicon member 11, as shown in FIG. 1. The dead wells 20–23 and the driven wells 24–27 are preferentially etched in the silicon member 11 so as to provide very thin (not greater than 100 $\mu$m) walls or membranes of silicon indicated at 31 and 32 in FIG. 2. The fill wells, dead wells, and driven wells may be of a square, rectangular, octagonal, or circular configuration and taper as indicated at 33 from the inner surface of silicon member 11 to the thin wall or membrane of the silicon member, see FIG. 2. As an option, a fill pipe or tube 34, only one shown, may be inserted into the fill wells 16–19, with the end of the fill pipe configured to correspond to the configuration of the fill wells. When a silicon nitride (SiN) or silicon cap layer is used on the upper surface of member 11, the silicon wall or membrane 32 of the driven wells may be very thin, even zero in thickness, since the SiN or cap layer provides the needed strength.

The silicon member 11 is anodically bonded to the glass substrate 10, as indicated at 35 in FIG. 2, and the anodic bonding will sustain pressures in excess of 1.4 MPa (200 psi). As shown in FIG. 1 the capillaries (chemical jets) 12–15 are constructed to be focused on a point 42 but may be parallel, as discussed above.

A plurality of acoustic transducers, such as piezoelectric drivers 36, 37, 38, and 39 are mounted on an upper surface of silicon member 11 over the driven wells 24–27, as shown in FIGS. 1 and 2. The piezoelectric drivers are each connected via electrical leads 40 and 41 to a power supply computer control system not shown. Details of the piezoelectric drivers are set forth hereinafter in the description of FIG. 4. Actuation of the piezoelectric driver 39, for example, forced fluid in capillary 15 from orifice 30 producing a fluid (chemical) droplet, see FIG. 2, at focus point 42, see FIG. 1.

While the capillaries 12–15 are shown as being etched in the substrate 10, they can be etched into the lower surface of silicon member 11, or in both member 11 and substrate 10. This can be done in a manner that allows for atomically smooth inside surfaces, and so sharp concave regions and material roughness won't tend to trap bubbles when "priming" the pump (prior to activation of the piezoelectric drivers).

As pointed out above, where a silicon nitride layer is positioned above the driven wells 24–27, the silicon of member 11 can be fully or near fully etched away (stopping at the silicon nitride layer), such that the membranes 32, see FIG. 2, are eliminated or are very thin. The point is that the membrane region under the piezoelectric driver can be very thin, i.e., compliant but yet very strong and chemically resistant. This allows for optimal driver deformation of the membrane and efficient compression of the fluid in the driven well.

A key feature of the invention is in the capillary arrangement, wherein the capillary path length from the driven well to the exit is short (20 to 2,000 $\mu$m) and has a width of 10 to 200 $\mu$m. The length from the driven well to the dead well is longer (1 to 100 mm) and is narrower in diameter (width of 10 to 50 $\mu$m). When the driven well is compressed, the fluid is more easily ejected out the nozzle. The dead well acts as a large inertial mass to prevent backfiring; this geometry promotes a one-way pumping action with no moving (i.e., sliding, flapping) parts. This provides a big advantage in microfluidics because flapping valves and sliding parts tend to clog with very small particulates and contaminants for very small fluid samples. Also, trapping of microbubbles is greatly reduced. This is essentially a pump with no moving parts: a one way fluid motion provided by: a) the preferential fluid flow system, and b) the fact that after a drop exits the nozzle with some velocity and pinches off, there is no backflow possible. The fluid flow is preferential because of the flow channel and driver design, both of which are assymetrical.

The capillaries tend to naturally be refilled by capillary surface tension (liquids tend to get sucked up by small capillaries). So the system ejects a drop quickly; then the exit capillary likes to refill itself, and it does this slowly from the entire fluid path (fill well, dead well, driven well). This can be enhanced by a net pressure on the fill well. This is not a rapid rate system (compared to thermal ink jets which can heat and cool very quickly).

The preferred capillary design incorporates three different capillary diameters: large (200 to 1,000 $\mu$m) from the fill well to the dead well (rapid refill, low flow resistance). Small (10 to 50 $\mu$m) and long (1 to 100 mm) from the dead well to driven well (high flow resistance). Medium (20 to 200 $\mu$m) and short (20 to 2,000 $\mu$m) from the driven well to the exit nozzle (low flow resistance, but still smaller enough diameter to make microdrops).

It is very feasible to put a common manifold over the driven well membranes and then drive (pressurize) this manifold from one source. The same pressure would be applied to all driver membranes (which have very high uniformity, like the capillary channels); the drops could all be ejected simultaneously from one drive signal. Of course, for some applications, the drivers are driven independently. But if not, a common manifold may be cheaper and more practical, wherein one pressure manifold pressurizes all the driven well membranes simultaneously.

The piezoelectric bimorph, such as illustrated in FIG. 4, may be designed to allow the membrane over the driven well to deform up (suction) as well as down (compression). This would allow the micronozzle to suck up slowly, with excellent control, a microdroplet or microsample sitting on a surface or a controlled portion of the microdroplet; move the dispenser; and then eject the microsample (or a portion of it) quickly. This essentially would use the dispenser as a microdrop transfer device.

FIG. 3 is an enlarged cross-sectional view of an embodiment of the silicon member 11 of FIG. 1, showing the various layers thereof, some of which may be optional. As shown, substrate 10 is bonded to silicon member 11 at 35, with a fill well 19, dead well 23, and driven well 27 formed in member 11 so as to form membranes or walls 31 and 32; wells 19 and 23 being connected by orifice 28, wells 23 and 27 connected by orifice 29, and well 27 connected to an exit orifice or nozzle 30 by which a droplet 42 is formed, as in the FIG. 1 embodiment. As seen in FIG. 3, a silicon nitride (SiN) layer 43 is deposited on the upper surface of silicon member 11, the piezoelectric (ultrasonic) driver 39 being secured by a conductive epoxy to SiN layer 43 via a pad 44 such as gold. A dead well support or layer 45, constructed of glass, for example, is secured to layer 43 over dead well 23 to strengthen the thin membrane 31, if necessary. The more compliant the membrane 31 is, the more effective it can be as a backfire absorber. Acoustic absorber layers 46 and 47 are deposited on a lower surface of substrate 10 and on the surface of SiN layer 43 in the area of the dead wells and the driven wells, while not covering the drivers 39 as shown in FIG. 3. The acoustic absorber layer 47 may cover the dead well support 45 for backfire absorption.

FIG. 4 is an enlarged cross-sectional view of a two layer PZT bimorph (piezoelectric driver) as mounted on the dispenser of FIG. 1, for example. A silicon member 11' is bonded to a glass substrate 10' having a capillary 12' therein. Silicon member 11' is etched to form a driven well 24' having a thin membrane or silicon wall 32'. For example, the glass substrate 10' is 1 mm thick Pyrex and the silicon member 11' is 0.375 mm thick, with the membrane or wall 32' being 10×10×0.040 mm, with the well 24' having a bottom length and width of about 10 mm and an upper length and width of about 9.0 mm with a taper 33' of 57°. The taper of 57° is the anisotropic etch angle of the {111} and {100} crystal planes of silicon, conventionally illustrated at 45°, for convenience. The piezoelectric driver 36' is a 12×12×0.4 mm PZT (lead zirconium titanate) bimorph composed of layers or plates PZTa and PZTb bonded to the surface of silicon member 11' by epoxy as indicated at 48. The PZTa layer is also edge sealed to the silicon member 11' by a sealing epoxy 49. The layers or plates PZTa and PZTb are bonded as indicated at 50 so as to be oppositely poled (the poling axes are head to head). Plate PZTa, for example, is straight when unbiased, but when biased by passage of an electrical field therethrough, it expands laterally and shrinks vertically; while plate PZT b has a similar polarity electric field bias and a subsequent lateral shrinkage. With PZTa expanding and PZTb shrinking, the bimorph bulges downward into the driven well, thus reducing its volume.

While the piezoelectric drivers are preferably PZT bimorphs, they can be constructed of a single or of multiple PZT layers or plates. However, for the application here, tests have shown that the composite as illustrated in FIG. 4 is the most effective for producing drop-by-drop or continuous flow of fluid from the driven wells. As set forth above, the PZT layers or plates may be constructed to produce a double action (forward and reverse) pumping arrangement.

The present invention has been experimentally tested using a round configuration having six (6) capillaries in the glass substrate and using a 75 mm diameter (3 inch) silicon wafer on which the fill wells, dead wells, and driven wells were etched; and fabrication of the prototype is described as follows:

I. Photolithographic Masking

The prototype device was fabricated with the use of three photolithographic masking layers: 1) the first layer was used to pattern the silicon on the on the inside or bonded side with a deep timed etch to make the fluid wells in the silicon; 2) the second layer was to pattern a gold layer onto the outer silicon surface, and it was registered with the first layer so as to be above the driven wells; and 3) the third layer was used to define the six capillaries in the glass substrate; and each had varying diameters from the feed section (large ~400 μm), to the middle section (small ~20 μm), to the nozzle section (medium ~100 μm).

II. Silicon Processing

The silicon starting material was [100] oriented with standard wafer flats and was double side polished and 375 μm thick. The following is a brief outline of a typical fabrication sequence for the silicon part of the device.

SILICON PROCESS SEQUENCE:
1. Clean the silicon wafers—RCA clean.
2. CVD deposit masking nitride. 100 nm low stress silicon nitride.
3. Coat with HMDS adhesion promoter.
4. Print layer one; the silicon well patterns. Shipley 1518 positive resist, 1 μm thick.
5. Plasma etch layer one features into silicon nitride (etch windows); $CF_4/O_2/200$ mT/150 W.
6. Timed KOH etch of silicon to form reservoirs and actuator membranes and inlet ports. Done in three steps with intermediate depth measurements to estimate finish time when silicon membrane is 40 μm thick.
7. Strip the remaining silicon nitride mask.
8. Coat with HMDS adhesion promoter.
9. Spin coat with Shipley 1518 positive resist, 1 μm thick, in special spinning jig with retaining pins around the periphery, not using vacuum clamp because of the membranes. Soft bake.
10. Use special double sided alignment jig: align layer two mask to layer one mask in jig.
11. Print layer two: align wafer etched features from layer one to layer one mask; assemble prealigned jig and print layer two. When drying wafers after development and rinse, use special care with air drying nozzle; use at low pressures and angle shallow enough to prevent blowing Si windows in, or creating a Bernoulli effect and sucking them out.
12. E-beam evaporate layer two metals for outside locators (inlet ports, dead wells, and wafer precision saw lines, and PZT pads): 10 nm Cr then 100 nm Au.
13. Liftoff in hot acetone and ultrasonic. Use Q tip in hot (boiling) acetone to scrub the metal that is not "lifted off", but very carefully avoid the silicon membranes. The e-beam coater tends to overheat the photoresist, impeding lift off.
14. Rinse in isopropyl alcohol and water. Blow dry.

III. Glass Processing

The glass for the device was the Corning 7740 type, commonly known as Pyrex. This glass is designed to have a similar thermal expansion coefficient to the silicon and is also useful for anodic bonding. The glass wafers used for this project were double side polished by an optical supplier to an optical finish from the manufacturer's blanks; the original thickness was about 3 mm and the final size is 1 mm thick and 75 mm in diameter.

GLASS PROCESS SEQUENCE:
1. Clean the glass wafers; organic removal: hot peroxide/ sulfuric; water rinse.
2. Sputter coat the glass, capillary side, with 100 nm Mo at low power (low stress).
3. Print layer three; the capillaries.
4. Etch the capillary patterns into the Mo; $35H_3PO_4/35H_2O/20Acetic/10HNO_3$.
5. Strip the photoresist.
6. Etch the capillaries into the glass; $40HF/40HCl/20H_2O$; patterned Mo mask.
7. Strip the Mo.
8. Water rinse, blow dry.

IV. Piezoelectric Processing

The piezoelectric actuator was made from commercial PZT (Lead Zirconium Titanate) plates that were silver plated and poled; the plates were 225 μm thick and 25 mm square.

PZT PROCESS SEQUENCE:
1. First, the poling polarity must be determined. This is easily done by placing the PZT plate on a simple jig made with an aluminum foil covered microscope slide and a spring contact. The bottom side of the plate contacts the foil which is used as electrical ground. The top side of plate is contacted by a spring contact that is connected to an oscilloscope. With the oscilloscope scanning at about a one second rate and a vertical sensitivity of about 0.1 V/cm, the plate is mechanically tapped gently with a small tool, such as a rounded cap end of a ball point pen. The PZT is very fragile and prone to cracking if sharp tools, or deforming forces are used. The compressive force of the tool impact generates a bipolar pulse whose initial portion is positive when the top side is oriented correctly; this side is then marked positive.

2. The PZT bimorph can be formed by bonding together two PZT plates with opposing poling polarities, either head to head or tail to tail. Either method can work, but the bending motion (a dome like bulge of the bimorph plate) from an applied field will have opposing polarities, so it is very important to keep track of the polarities throughout. The bonding is accomplished using silver conductive epoxy, spread onto the plates with a wooden toothpick to several hundred microns thick. The two plates are then brought into contact. The excess epoxy is initially squeezed out by hand pressure, starting at the center, and then removed with a Q tip; the plate pair is finally pressured between two glass plates that are covered with wax paper and squeezed again with hand pressure of several pounds force. A curing weight of about 600 g is applied to composite plate stack. This results in an epoxy bond layer about 100 $\mu$m thick.

3. The bonded plates are now shorted on the sides by the excess epoxy. The square actuators and test cantilever beams are cut from the bonded pair with a precision abrasive saw that is water cooled. The edges of the bimorph are now clean and free from any silver or epoxy that might short out the device. These edges must be kept clean and free from fingerprints, etc., to prevent arc formation from high bias voltages.

4. The polarity of the bonded pair is determined before edge sealing and mounting onto the anodically bonded silicon/glass composite. The bonded pair test is also determined with a very simple, but different clamping jig. This jig is again made with an aluminum foil covered microscope slide. The PZT bimorph is placed on the slide so that about 1.5 mm of it is off the end of the foil, but still over the glass. This portion is then clamped with a small alligator clip, bent so that it contacts the upper bimorph electrode; the lower bimorph electrode is contacted by contacted by the aluminum foil at its edge. This leaves the entire bimorph, mounted like a diving board, tilting slightly off but still over the foil covered slide. See FIG. 5.3. The free end, opposite the alligator clip clamp, is placed under a microscope. By applying voltages from ten to several hundred volts across the bimorph, the end of the device deflects under the microscope. With a high magnification, the depth of field is very shallow, and the vertical position of the free end of the bimorph can be determined as a function of voltage. The polarity of the composite is again marked with a pencil on the silver plating, so that it is clear which side of the composite must have a certain polarity voltage in order to deform in a convex fashion.

5. The sides of the bimorph are now coated with a thin layer of clear, non conductive epoxy. This is done by first generating some of the epoxy in a very thin layer on a microscope slide, using another slide as a squeegee. Then the bimorph is held by a small vacuum chuck and contacted into the thin layer, edge-on, sequentially on all four sides. After the clear epoxy is placed on all four edges, the bimorph is pressed against a wax paper protected glass plate. This last procedure should leave the mounting side of the bimorph flat, so that its silver plating can be bonded to the gold plated silicon pad; the sides should be well protected from shorting out in the final conductive epoxy mounting procedure to the silicon and also protected from shorting out or arcing along the edges of the bimorph. One final deflection and polarity check is done to confirm the absence of shorts and correct polarity.

V. Bonding and Final Assembly

1. The silicon and glass wafers were anodically bonding together at 450° C. in a nitrogen atmosphere. First, alignment is done under a low power microscope by hand and pressure is applied until interference fringes are observed. With a successful anodic bond, the silicon actuator diaphragms are visibly bowed inwards about 100 $\mu$m by the atmospheric pressure during the cool down. The entire capillary system and fluid cavities are under partial vacuum and a leak free channel is obvious. The yield for this procedure was 100% for about six wafer pairs with six channels per wafer. The inlet port is now opened by forcing a syringe tip into the silicon membrane in the inlet port region; the hole is enlarged using the beveled edge of the syringe tip. The debris is lightly shaken loose, but the excess small silicon debris is not blown off or washed out at this stage to prevent it from jamming in the inlet capillary. The composite wafer pair is now cut on a water cooled precision wafer saw to form the exit nozzles; the gold reference cut lines on outer silicon side are used for saw alignment. The robust glass outer bottom side is used for adhesive mounting to the saw table. After the sawing, the wafer composite is ultrasonically washed in water and isopropyl alcohol to remove saw and silicon debris from the previous steps. The alcohol is finally removed from the interior of the device by placing it at an approximately 30 degree incline under an incandescent desk lamp to provide a slow drying situation with a modest temperature and gravimetric gradient.

2. The PZT bimorph is bonded onto the silicon side of the silicon/glass wafer pair with silver conductive epoxy. A vacuum chuck is used. The bimorph is pressed and laterally moved very slightly to thin the conductive epoxy; it is very important to get the epoxy thin for good transducer coupling, while not shorting out the insulating protective side walls of the bimorph. At the same time, small electrical leads can be epoxied onto the bimorph ground plane pad and also onto the top of the bimorph, using a minimal mass.

3. The dead wells are capped on the outside with clear epoxy using 12 mm square pieces of glass. This is to protect the dead well from bursting during priming/purging operations.

4. The inlet to the wafer pair is done with standard syringe needle where the end has been filed to a very blunt bevel, with the opening facing the channel. The needle is supported by an aluminum cylindrical ferrule, with a loose sliding fit over the needle. The inlet connection takes three sequential epoxy joints. First, the ferrule is coated with a very small amount of epoxy on its outer cylindrical edge, near the bottom, but not on the bottom itself. If epoxy is on the bottom face of the ferrule, it will ooze into the inlet port and block it. The ferrule is slid high onto the needle, then the needle is put into the inlet port on the wafer, then the ferrule is released to slide down the needle and make contact with the wafer. The epoxy will make a small fillet on the outside of the cylinder as the ferrule is rotated, while the needle is used to position the assembly. After the ferrule epoxy is cured, the needle can be epoxied onto the top of the ferrule. Finally, a third coating of epoxy can be applied to both joints as a thick supportive layer, now that the parts are sealed and in the correct placement.

It has thus been shown that the present invention provides a fluid dispenser which does not heat the sample fluids and is constructed by micromachining technology which enables the production of large arrays (~100–200 capillaries), as well as dense linear arrays (~50 channels/cm) in a manner that is stackable, thus further enabling the generation of two dimensional arrays of chemical samples, with micron precision; droplets in the range of 10–200 $\mu$m are feasible. The invention provides several function capabilities, including: a one way pump, a valveless pump, common drive manifold, and drop transfer operation. The efficiency of this drop dispensing device is much greater than current non-monolithic technologies can allow, and it is ideally suited to computer control and robotics systems.

While particular embodiments have been described and/or illustrated, with particular materials, parameters, etc., such are not intended to be limiting. Modifications and changes may become apparent to those skilled in the art, and it is intended that the invention be limited only by the scope of the appended claims.

The invention claimed is:

1. A fluid dispenser, comprising:

a substrate, a member bonded to said substrate, at least one ultrasonic transducer, said substrate being provided with at least one capillary having one end at one edge of said substrate, said member being provided with at least one fill well, at least one dead well, and at lease one driven well, said wells in said member being aligned with an in fluid communication with said at least one capillary in said substrate, and said at least one ultrasonic transducer being positioned over said at least one driven well, whereby actuation of said transducer forces fluid from said at least one driven well and out said one end of said at least one capillary.

2. The fluid dispenser of claim 1, wherein said at least one capillary has a diameter of 10–200 $\mu$m.

3. The fluid dispenser of claim 1, wherein said at least one fill well is constructed to include an opening in an upper surface of said member.

4. The fluid dispenser of claim 1, wherein each of said at least one dead well and at least one driven well includes a thin membrane adjacent an upper surface of said member.

5. The fluid dispenser of claim 1, wherein said at least one ultrasonic transducer comprises a piezoelectric driver.

6. The fluid dispenser of claim 1, wherein said member is provided with a layer of acoustic absorption material on at least one surface thereof.

7. The fluid dispenser of claim 1, wherein said member is provided with a layer of strengthening material over at least said dead well and said driven well.

8. The fluid dispenser of claim 1, wherein said substrate is composed of material selected from the group consisting of glass, quartz, and metal; and wherein said member is composed of material selected from the group consisting of silicon, germanium, and gallium arsenide.

9. The fluid dispenser of claim 8, wherein said member is composed of silicon, and additionally including a layer of material on an upper surface of said silicon member selected from the group of silicon and silicon nitride.

10. The fluid dispenser of claim 8, additionally including a glass support layer positioned over at least said at least one dead well.

11. The fluid dispenser of claim 1, wherein each of said fill well, said dead well, and said driven well are formed in said member to have a configuration selected from the group consisting of square, rectangular, and circular.

12. The fluid dispenser of claim 11, wherein each of said wells include a tapering section with a larger diameter thereof on a surface of said member adjacent said substrate.

13. The fluid dispenser of claim 1, additionally including a fill tube positioned in said at least one fill well.

14. The fluid dispenser of claim 1, wherein said substrate is provided with a number of capillaries, and wherein said member is provided with a number of sets of fill wells, dead wells, and driven wells, each set being aligned with a capillary on said substrate.

15. The fluid dispenser of claim 1, being constructed to enable stacking thereof.

16. A micromachined chemical jet dispenser, comprising:

a glass substrate having a number of capillaries formed thereon, a silicon member bonded to said glass substrate and having a number of sets of fill wells, dead wells, and driven wells formed therein, each set being aligned with and in fluid communication with a capillary on said glass substrate, and a number of ultrasonic transducers positioned on said silicon member over said number of driven wells, whereby actuation of said transducers dispenses fluid from said capillaries.

17. The dispenser of claim 16, wherein said transducers can be actuated to produce a continuous flow or drop-on-demand of fluid from one or more of said capillaries.

18. The dispenser of claim 16, wherein said dead wells and said driven wells are constructed in said silicon member so as to define a thin wall of silicon at an upper surface of said silicon member.

19. The dispenser of claim 16, wherein said fill wells are constructed in said silicon member so as to define an opening extending through the silicon member.

20. The dispenser of claim 16, wherein said transducers are composite actuators driven by piezoelectric effect.

* * * * *